US010569259B2

(12) United States Patent
Choi et al.

(10) Patent No.: US 10,569,259 B2
(45) Date of Patent: *Feb. 25, 2020

(54) CATALYST FOR DEHYDRATION OF GLYCERIN, PREPARATION METHOD THEREOF, AND PRODUCTION METHOD OF ACROLEIN USING THE CATALYST

(71) Applicant: LG CHEM, LTD., Seoul (KR)

(72) Inventors: Jun Seon Choi, Daejeon (KR); Ji Yeon Kim, Daejeon (KR); Joo Young Cheon, Daejeon (KR); Wang Rae Joe, Daejeon (KR); Hye Jeong Ok, Daejeon (KR); Kyung Soo Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/749,472

(22) PCT Filed: Dec. 15, 2016

(86) PCT No.: PCT/KR2016/014741
§ 371 (c)(1),
(2) Date: May 29, 2018

(87) PCT Pub. No.: WO2017/111392
PCT Pub. Date: Jun. 29, 2017

(65) Prior Publication Data
US 2018/0257063 A1 Sep. 13, 2018

(30) Foreign Application Priority Data

Dec. 22, 2015 (KR) ........................ 10-2015-0184168
Oct. 7, 2016 (KR) ........................ 10-2016-0129986

(51) Int. Cl.
C07C 45/52 (2006.01)
B01J 27/00 (2006.01)
B01J 23/00 (2006.01)
B01J 21/00 (2006.01)
B01J 27/18 (2006.01)
B01J 37/08 (2006.01)
B01J 37/06 (2006.01)
B01J 27/185 (2006.01)
B01J 27/188 (2006.01)
B01J 37/03 (2006.01)
B01J 27/195 (2006.01)
B01J 35/10 (2006.01)
C07C 47/22 (2006.01)

(52) U.S. Cl.
CPC ......... B01J 27/1808 (2013.01); B01J 23/002 (2013.01); B01J 27/188 (2013.01); B01J 27/1853 (2013.01); B01J 27/195 (2013.01); B01J 35/1014 (2013.01); B01J 35/1019 (2013.01); B01J 37/031 (2013.01); B01J 37/06 (2013.01); B01J 37/08 (2013.01); B01J 37/088 (2013.01); C07C 45/52 (2013.01); C07C 47/22 (2013.01); B01J 2523/00 (2013.01)

(58) Field of Classification Search
CPC ....... C07C 45/52; B01J 27/1808; B01J 21/06; B01J 23/002
See application file for complete search history.

(56) References Cited

U.S. PATENT DOCUMENTS

| 6,545,177 | B2 | 4/2003 | Tanimoto et al. |
| 7,396,962 | B1 | 7/2008 | Dubois et al. |
| 7,683,220 | B2 | 3/2010 | Matsunami et al. |
| 8,252,960 | B2 | 8/2012 | Dubois et al. |
| 8,829,246 | B2 * | 9/2014 | Dubois ............... C07C 45/52 568/486 |
| 8,962,881 | B2 | 2/2015 | Tanimoto et al. |
| 9,079,847 | B2 | 7/2015 | Kelliher et al. |
| 9,296,676 | B2 | 3/2016 | Devaux et al. |
| 9,321,040 | B2 | 4/2016 | Joe et al. |
| 9,327,276 | B2 | 5/2016 | Choi et al. |
| 9,447,009 | B2 | 9/2016 | Belliere-Baca et al. |
| 2008/0146852 | A1 | 6/2008 | Dubois et al. |
| 2008/0214384 | A1 | 9/2008 | Redlingshofer et al. |
| 2009/0069586 | A1 | 3/2009 | Oku et al. |
| 2010/0298601 | A1 | 11/2010 | Choi et al. |

(Continued)

FOREIGN PATENT DOCUMENTS

| EP | 2377842 A1 | 10/2011 |
| EP | 3189892 A1 | 7/2017 |

(Continued)

OTHER PUBLICATIONS

Chai, et al., "Sustainable production of acrolein: Preparation and characterization of zirconia-supported 12-tungstophosphoric acid catalyst for gas-phase dehydration of glycerol", Applied Catalysis A: General, vol. 353, pp. 213-222 (2009).
Gan, et al. "Gas phase dehydration of glycerol to acrolein catalyzed by zirconium phosphate", Chinese Journal of Catalysis, vol. 35, pp. 1148-1156 (2014).
Rao, et al.: "Porous zirconium phosphate supported tungsten oxide solid acid catalysts for the vapour phase dehydration of glycerol", Journal of Molecular Catalysis A: Chemical, Elsevier Science Publishers B.V., vol. 395, Sep. 28, 2014, pp. 486-493.
Lauriol-Garbey, et al, "New efficient and long-life catalyst for gas-phase glycerol dehydration to acrolein", Journal of Catalysis, vol. 281, No. 2, pp. 362-370 (2011).

(Continued)

Primary Examiner — Sikarl A Witherspoon
(74) Attorney, Agent, or Firm — Dentons US LLP

(57) ABSTRACT

The present disclosure relates to a catalyst for dehydration of glycerin, a preparation method thereof, and a production method of acrolein using the catalyst.
Particularly, the catalyst according to an embodiment of the present disclosure is used in a dehydration reaction of glycerin to exhibit high catalytic activity, a high yield, and high selectivity to acrolein and acrylic acid, and has a longer lifetime compared to the conventional catalysts due to a characteristic that coke carbon cannot be easily deposited on the surface of the catalyst.

10 Claims, 2 Drawing Sheets

(56) References Cited

U.S. PATENT DOCUMENTS

| | | |
|---|---|---|
| 2011/0213174 A1 | 9/2011 | Dubois |
| 2011/0288323 A1 | 11/2011 | Belliere-Baca et al. |
| 2013/0018161 A1 | 1/2013 | Ezawa et al. |
| 2013/0053595 A1 | 2/2013 | Magatani et al. |
| 2013/0066100 A1 | 3/2013 | Magatani et al. |
| 2013/0303801 A1 | 11/2013 | Ueda et al. |
| 2014/0206527 A1 | 7/2014 | Okumura et al. |
| 2017/0304804 A1 | 10/2017 | Kim et al. |

FOREIGN PATENT DOCUMENTS

| | | |
|---|---|---|
| JP | 2007-137785 A | 6/2007 |
| JP | 4041512 B2 | 1/2008 |
| JP | 2010-516462 A | 5/2010 |
| JP | 2011518111 A | 6/2011 |
| JP | 2012-512236 A | 5/2012 |
| JP | 2013508127 A | 3/2013 |
| JP | 5450591 B2 | 3/2014 |
| JP | 5702205 B2 | 4/2015 |
| JP | 5784609 B2 | 9/2015 |
| KR | 100264966 B1 | 9/2000 |
| KR | 101043400 B1 | 6/2011 |
| KR | 1020110094198 A | 8/2011 |
| KR | 1020120093853 A | 8/2012 |
| KR | 101248262 B1 | 3/2013 |
| KR | 1020130111230 A | 10/2013 |
| KR | 1020140015349 A | 2/2014 |
| KR | 1020140053209 A | 5/2014 |
| KR | 1020150009452 A | 1/2015 |
| KR | 1020150037479 A | 4/2015 |
| KR | 101541934 B1 | 8/2015 |
| KR | 10-2017-0057706 A | 5/2017 |
| WO | 2012005348 A1 | 1/2012 |
| WO | 2012101526 A1 | 8/2012 |
| WO | 2013008279 A1 | 1/2013 |
| WO | 2016/099066 A1 | 6/2016 |
| WO | 2017/111391 A1 | 6/2017 |

OTHER PUBLICATIONS

Katryniok, et al.; "Recent Developments in the Field of Catalytic Dehydration of Glycerol to Acrolein", ACS Catalysis, vol. 3, No. 8, pp. 1819-1834 (2013).

Rajan, et al., "Vapour phase dehydration of glycerol over VPO catalyst supported on zirconium phosphate", Catalysis Science & Technology, vol. 4, No. 1, pp. 81-92 (2014).

* cited by examiner

[FIG. 1]
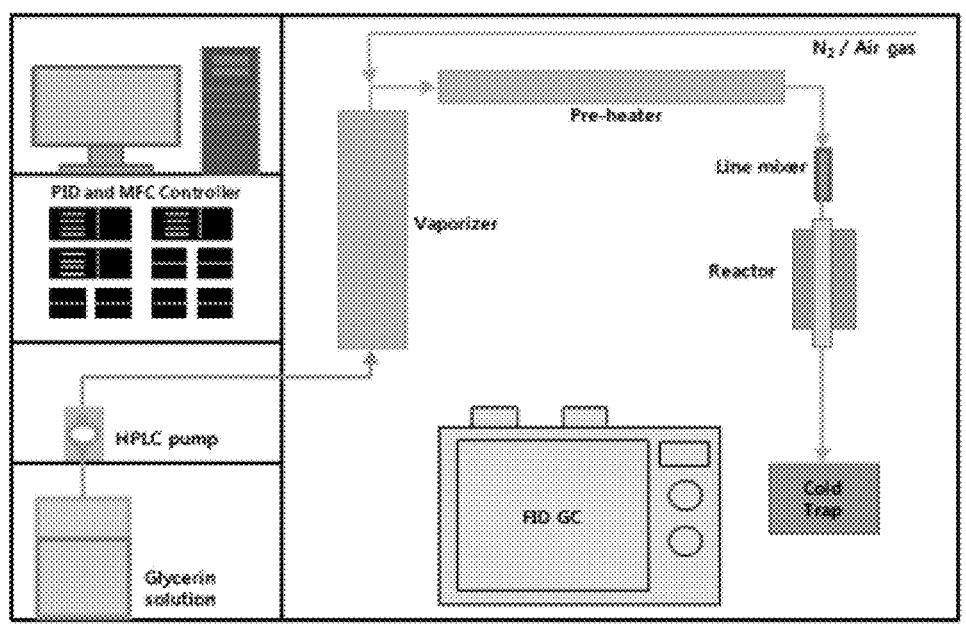

[FIG. 2]
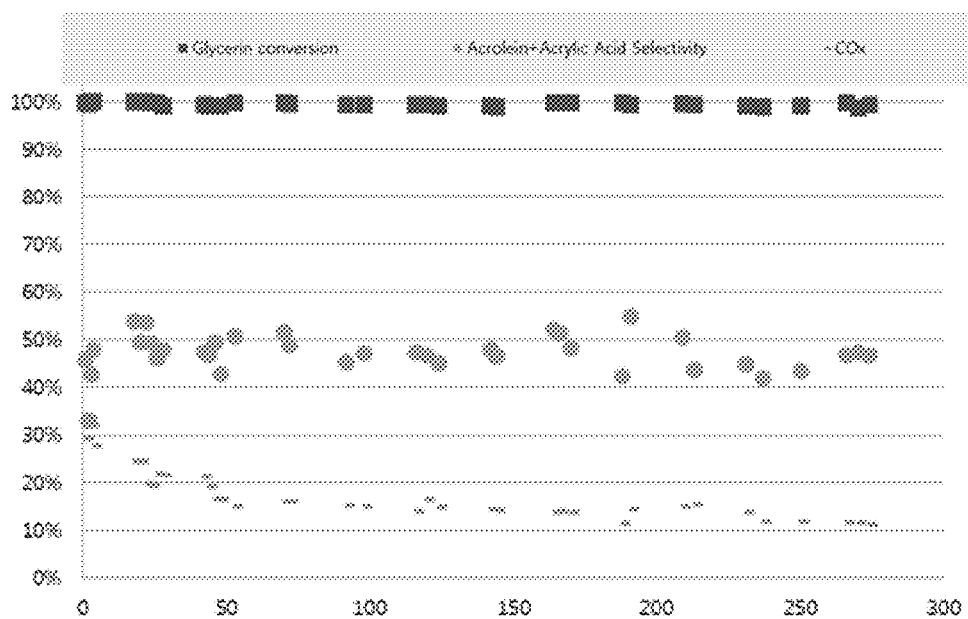
[FIG. 3]
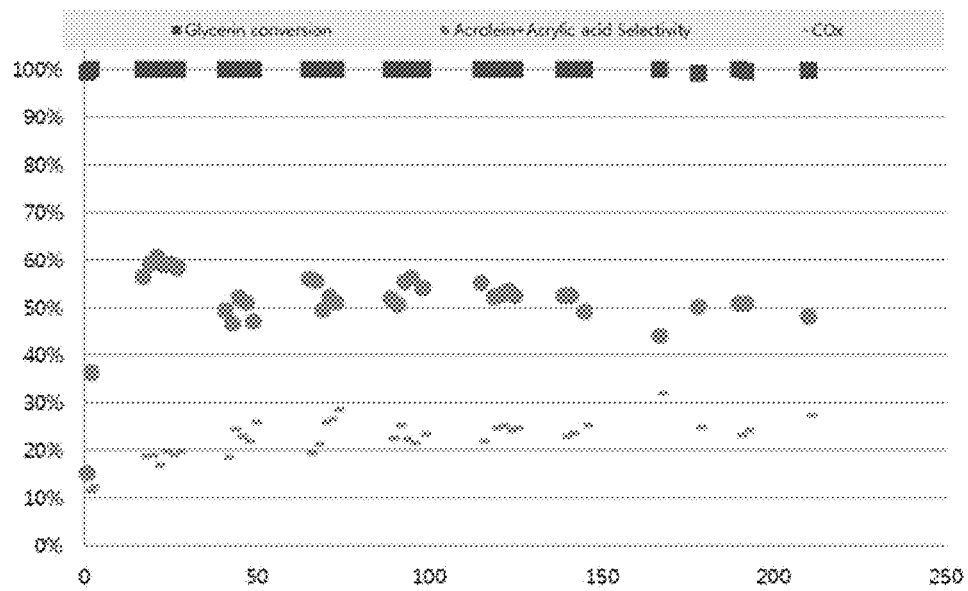

US 10,569,259 B2

CATALYST FOR DEHYDRATION OF GLYCERIN, PREPARATION METHOD THEREOF, AND PRODUCTION METHOD OF ACROLEIN USING THE CATALYST

CROSS-REFERENCE TO RELATED APPLICATIONS

This application is a National Stage Application of International Application No. PCT/KR2016/014741, filed Dec. 15, 2016, and claims the benefit of Korean Patent Application No. 10-2016-0129986, filed Oct. 7, 2016, Korean Patent Application No. 10-2015-0184168, filed Dec. 22, 2015 contents of which are incorporated herein by reference in their entirety for all purposes as if fully set forth below.

TECHNICAL FIELD

The present disclosure relates to a catalyst for dehydration of glycerin, a preparation method thereof, and a production method of acrolein using the catalyst.

BACKGROUND OF THE INVENTION

Acrolein is a simple unsaturated aldehyde compound which includes incomplete reactive groups to have high reactivity, and is used as a major intermediate for synthesis of numerous chemicals. In particular, acrolein has been widely used as an intermediate for synthesis of acrylic acids, acrylic acid esters, superabsorbent polymers, animal feed supplements, or food supplements.

Such acrolein has been mainly prepared by selective gas-phase oxidation of a starting material, propylene, which is obtained during petroleum cracking, with atmospheric oxygen. However, as fossil fuels have been reduced and environmental problems such as the greenhouse effect have emerged, many studies have been conducted to develop a method of preparing acrolein using non-fossil fuel-based renewable materials.

Therefore, glycerin, which is a natural by-product obtained from biodiesel production, has received much attention as a raw material for acrolein preparation. In particular, the growth of biodiesel production increases the size of the glycerin market, and industrial application of glycerin has been studied due to its low price.

For example, a method of obtaining a mixture of acrolein and acrylic acids by glycerin dehydration in the presence of a catalyst is known. The dehydration reaction of glycerin proceeds in a gas phase oxidation reaction in the presence of a catalyst, and the use of a catalyst is essential.

However, there is a problem that the catalyst is deactivated, because by-products such as hydroxypropanone, propane aldehyde, acetaldehyde, polycondensation products of glycerin, cyclic glycerin ether, phenol, or polyaromatic compound are formed as the dehydration reaction of glycerin proceeds, and then coke carbon is deposited on the catalyst. Therefore, efforts have been made to develop a catalyst having an increased lifetime that may be continuously operated by inhibiting deposition of the coke carbon.

Accordingly, there is a need to develop a catalytic reaction system capable of removing coke carbon so as to minimize the production of by-products which generate coke carbon or to maintain the activity of the catalyst during the reaction.

DETAILS OF THE INVENTION

Objects of the Invention

The present disclosure provides a catalyst for dehydration of glycerin and a preparation method of the same having an increased lifetime by inhibiting deposition of coke carbon or removing the coke carbon during the dehydration reaction of glycerin, and exhibiting high selectivity and efficiency to acrolein and acrylic acid.

The present disclosure also provides a production method of acrolein using the catalyst.

Means for Achieving the Object

According to an embodiment of the present disclosure, a catalyst for dehydration of glycerin represented by the following Chemical Formula 1 is provided.

$$Zr_a(M^1)_b(M^2)_cW_dP_eH_xO_y \qquad \text{[Chemical Formula 1]}$$

In Chemical Formula 1, $M^1$ and $M^2$ are the same as or different from each other, and are independently V, Fe, Nb, Zn, or a combination thereof; a, b, c, d, and e represent ratios of atoms, wherein a is 0.1 to 6, b/a is 0 to 1, c/a is 0 to 1, d/a is 0 to 1, e/a is 0 to 10, provided that at least one of b and c is not 0; and x and y are values determined according to a bonding state of crystallization water, and are independently 0 to 10.

For example, a may be 0.5 to 1, b may be 0.01 to 0.3, c may be 0.01 to 0.3, d may be 0.01 to 0.3, and e may be 1 to 5.

More specifically, the catalyst represented by Chemical Formula 1 may be $ZrZn_{0.02}W_{0.1}P_2H_xO_y$, $Zr_{0.9}Fe_{0.1}W_{0.1}P_2H_xO_y$, $Zr_{0.9}V_{0.1}W_{0.1}P_2H_xO_y$, $Zr_{0.9}Nb_{0.02}Fe_{0.1}W_{0.1}P_2H_xO_y$, $Zr_{0.9}Zn_{0.02}Fe_{0.1}W_{0.1}P_2H_xO_y$, $Zr_{0.9}Zn_{0.02}V_{0.1}W_{0.1}P_2H_xO_y$, $Zr_{0.9}Zn_{0.02}V_{0.1}W_{0.1}P_2H_xO_y$, $Zr_{0.8}Zn_{0.02}(FeV)_{0.1}W_{0.1}P_2H_xO_y$, $Zr_{0.8}Zn_{0.02}Fe_{0.2}W_{0.1}P_2H_xO_y$, $Zr_{0.8}Zn_{0.02}V_{0.2}W_{0.1}P_2H_xO_y$, or $Zr_{0.95}Zn_{0.02}V_{0.05}W_{0.1}P_2H_xO_y$, wherein x may be 2 to 6, and y may be 1 to 3.

According to another embodiment of the present disclosure, a preparation method of a catalyst for dehydration of glycerin, including the step of mixing one or more precursors selected from the group consisting of the precursors of V, Fe, Nb, and Zn, a zirconium precursor, a phosphorus precursor, and a tungsten precursor, followed by drying and calcining to produce a catalyst represented by Chemical Formula 1, is provided.

The drying may be carried out at a temperature of 25 to 200° C., and for 3 to 48 hours. Further, the calcining may be carried out at a temperature of 250 to 750° C., and for 3 to 48 hours.

The mixture may be stirred for 3 to 48 hours. In addition, the precursor compound of the catalyst represented by Chemical Formula 1 may be precipitated from the mixed aqueous solution, and the precipitated catalyst precursor compound may be filtered and washed with water or an alcohol, followed by drying and calcining.

According to another embodiment of the present disclosure, a production method of acrolein, including the step of dehydration of glycerin in the presence of the catalyst for dehydration of glycerin, is provided.

Effects of the Invention

The catalyst according to an embodiment of the present disclosure is used in a dehydration reaction of glycerin to exhibit high catalytic activity, a high yield, and high selectivity to acrolein and acrylic acid, and has a longer lifetime compared to the conventional catalysts due to a characteristic that coke carbon cannot be easily deposited on the surface of the catalyst by burning and removing the produced coke carbon.

BRIEF DESCRIPTION OF DRAWINGS

FIG. 1 is a schematic diagram of an experimental apparatus according to an embodiment of the present disclosure.

FIG. 2 is a graph showing the performance of a reaction catalyst over time using a molded catalyst (diameter of 5 mm, length of 5-15 mm) according to Example 16 of the present disclosure, and an aqueous solution having a glycerin concentration of 50 wt %.

FIG. 3 is a graph showing the performance of a reaction catalyst over time using a molded catalyst (diameter of 5 mm, length of 5-15 mm) according to Example 17 of the present disclosure, and an aqueous solution having a glycerin concentration of 75 wt %.

DETAILED DESCRIPTION OF THE EMBODIMENTS

In the present disclosure, the terms "first", "second", and the like are used to describe a variety of components, and these terms are merely employed to differentiate a certain component from other components.

In addition, technical terms used in the present specification are only for explaining exemplary embodiments, and they are not intended to restrict the present invention. The singular expressions may include the plural expressions unless they are differently expressed contextually. It should be understood that the terms "include", "equip", "have", or the like are used to designate the existence of characteristics taken effect, numbers, steps, components, or combinations thereof, and do not exclude the existence or the possibility of addition of one or more different characteristics, numbers, steps, components of combinations thereof beforehand.

As the present invention may be variously modified and have various forms, specific examples will be explained in more detail. However, it is not intended to limit the present invention to the specific examples and it must be understood that the present invention includes every modifications, equivalents, or replacements within the spirit and technical scope of the present invention.

Hereinafter, a catalyst for dehydration of glycerin according to a preferable embodiment of the present disclosure, a preparation method thereof, and a production method of acrolein using the catalyst will be explained in more detail.

According to an embodiment of the present disclosure, a catalyst for dehydration of glycerin represented by the following Chemical Formula 1 is provided.

$$Zr_a(M^1)_b(M^2)_cW_dP_eH_xO_y$$ [Chemical Formula 1]

In Chemical Formula 1, $M^1$ and $M^2$ are the same as or different from each other, and are independently V, Fe, Nb, Zn, or a combination thereof, a, b, c, d, and e represent ratios of atoms, wherein a is 0.1 to 6, b/a is 0 to 1, c/a is 0 to 1, d/a is 0 to 1, e/a is 0 to 10, provided that at least one of b and c is not 0, x and y are values determined according to a bonding state of crystallization water, and are independently 0 to 10.

As described above, the dehydration of glycerin according to the conventional method causes the problem that the coke carbon is deposited on the catalyst as the reaction proceeds, thereby deactivating the catalyst and shortening the lifetime of the catalyst. Particularly, the acid catalyst having a large amount of BrØnsted acid sites has good production efficiency of acrolein among the known acid catalysts, but it is difficult to carry out the dehydration reaction for a long time, because the coke carbon is deposited on the catalyst during the dehydration reaction, and deactivating the catalyst easily.

In particular, conventional catalysts for production of acrolein and acrylic acid from glycerin form by-products such as hydroxypropanone, propane aldehyde, acetaldehyde, acetone, polycondensation products of glycerin, and cyclic glycerin ether. In addition, the conventional catalysts form phenol and polyaromatic compounds to deposit coke carbon on the catalyst, thereby causing deactivation. Deactivation of the catalyst makes it impossible to carry out the continuous operation of the dehydration reaction of glycerin, which makes commercialization difficult.

In addition, one of the major reasons of such catalyst deactivation is a loss of catalytic active sites due to deposition of coke carbon produced during the reaction. Particularly, factors affecting the formation of coke carbon in the dehydration reaction of glycerin are reaction conditions such as reaction temperature, space velocity, partial pressure of oxygen and steam in the reactant, mass transfer in the catalyst according to the pore structure of the catalyst, the amount of acid sites on the catalyst surface, the strength of acid sites, and the like. The acid sites of the catalysts are generally active sites for accelerating the dehydration reaction. However, when strong acid sites exist on the catalyst surface in excess, condensation between molecules due to side reactions leads to excessive formation of coke carbon precursors, and deactivation of the catalyst.

Therefore, the present disclosure may apply a specific catalyst composition in order to solve these conventional problems, and it may inhibit the formation of coke carbon during the reaction and effectively extend the lifetime of the catalyst. In particular, acrolein and/or acrylic acid may be obtained from glycerin in a high yield by using the catalyst capable of increasing the selectivity to acrolein and/or acrylic acid. The entire process efficiency may be remarkably improved by using the catalyst capable of removing the produced coke carbon to operate the glycerin dehydration reaction process continuously using a commercially available fixed bed reactor.

Acrolein may be obtained by dehydration of glycerin in the presence of an acid catalyst. Herein, it is known that the production efficiency of acrolein is good when a catalyst having more BrØnsted acid sites than Lewis acid sites is used as the acid catalyst. However, the acid catalyst having many BrØnsted acid sites has a problem in that carbon is deposited on the acid catalyst during the dehydration reaction, and is thus deactivated easily.

The catalyst represented by Chemical Formula 1 designed to solve the problem is a catalyst having the BrØnsted acid sites, but is not easily deactivated during the dehydration reaction of glycerin. In addition, the catalyst of Chemical Formula 1 has the BrØnsted acid sites and may exhibit a better yield of acrolein and catalytic activity than zirconium phosphate, which is known to have excellent catalytic activity.

For example, the catalyst of Chemical Formula 1 may have a in the range of 0.5 to 1, b in the range of 0.01 to 0.3, c in the range of 0.01 to 0.3, d in the range of 0.01 to 0.3, and e in the range of 1 to 5, in order to improve the yield of acrolein and catalytic efficiency compared with the conventional zirconium phosphate.

More specifically, the catalyst represented by Chemical Formula 1 may be $ZrZn_{0.02}W_{0.1}P_2H_xO_y$, $Zr_{0.9}Fe_{0.1}W_{0.1}P_2H_xO_y$, $Zr_{0.9}V_{0.1}W_{0.1}P_2H_xO_y$,

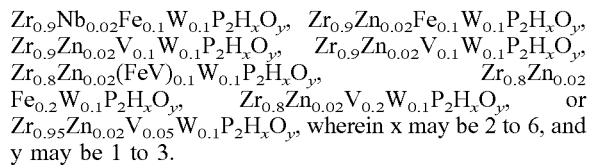
$Zr_{0.9}Nb_{0.02}Fe_{0.1}W_{0.1}P_2H_xO_y$, $Zr_{0.9}Zn_{0.02}Fe_{0.1}W_{0.1}P_2H_xO_y$, $Zr_{0.9}Zn_{0.02}V_{0.1}W_{0.1}P_2H_xO_y$, $Zr_{0.9}Zn_{0.02}V_{0.1}W_{0.1}P_2H_xO_y$, $Zr_{0.8}Zn_{0.02}(FeV)_{0.1}W_{0.1}P_2H_xO_y$, $Zr_{0.8}Zn_{0.02}Fe_{0.2}W_{0.1}P_2H_xO_y$, $Zr_{0.8}Zn_{0.02}V_{0.2}W_{0.1}P_2H_xO_y$, or $Zr_{0.95}Zn_{0.02}V_{0.05}W_{0.1}P_2H_xO_y$, wherein x may be 2 to 6, and y may be 1 to 3.

The mixed oxide may further include a metal represented by $M^1$ and $M^2$ in addition to zirconium, tungsten, and phosphorus. The $M^1$ and $M^2$ may inhibit formation of coke carbon and by-products, and deposition of coke carbon composed of phenol or polyaromatic compounds, which causes deactivation of the catalyst, because the metal may convert the generated coke carbon into a $CO_x$ material by inducing an oxidation reaction with oxygen or steam, and discharge it in a gas phase, to extend the lifetime of the catalyst.

The catalyst for dehydration of glycerin of the present disclosure may further include a support onto which the mixed oxide is immobilized. Any support that is known to be used in a typical catalyst may be used without limitations. Specific examples of the support may include silica, alumina, silica-alumina, zirconia, magnesia, magnesium aluminate, calcium aluminate, silicon carbide, zirconium phosphate, zeolite, or mixtures thereof. Preferably, silica having a pore size of 20 nm or more may be used.

The support may function to immobilize the mixed oxide of the embodiment, and the mixed oxide may be immobilized on the support with a large surface area by sharing oxygen therewith. When the mixed oxide is prepared by immobilizing it on the support, it is easier to store and transport, and then a large amount of glycerin may be effectively reacted due to the large surface area.

The support may have a specific surface area of 10 to 500 $m^2/g$, and preferably 50 to 200 $m^2/g$. In particular, the catalyst for dehydration of glycerin prepared by immobilizing the mixed oxide on the support having a large specific surface area within the above range has a proper pore size, thereby reducing coke deposition and providing sufficient catalytic activity.

The catalyst for dehydration of glycerin may include 1 to 50 parts by weight of the mixed oxide represented by Chemical Formula 1, based on 100 parts by weight of the support.

In addition, the catalyst for dehydration of glycerin of the present disclosure may be in a molded and assembled form to be used in a pilot process or a commercialized process. If a conventional catalyst in a powder form is used, the operation may not be performed properly because of a difference in internal pressure generated. Furthermore, such a molded catalyst may maintain the reaction activity for a long time by increasing the physical strength so as to not be cracked or damaged even when a large amount of the catalysts is laminated. Accordingly, inorganic materials, for example one or more fillers such as silica, alumina, titania, zirconia, and so on, may be added at the time of molding and assembling to increase the physical strength of the catalyst, and the catalyst may be manufactured through a calcination process at a high temperature. The molded and assembled catalyst may have a crushing strength of 25 N or more, or 25 N to 100 N, preferably 30 N or more, and more preferably 45 N or more, wherein the crushing strength is measured at the time when a crack occurs in a specimen of 0.5 mm in length and 0.5 mm in diameter using a compressive strength testing machine such as BOSS 5500.

According to another embodiment of the present disclosure, a preparation method of the catalyst represented by Chemical Formula 1 is provided. Specifically, the preparation method of the catalyst represented by Chemical Formula 1 includes the step of mixing one or more precursors selected from the group consisting of the precursors of V, Fe, Nb, and Zn, a zirconium precursor, a phosphorus precursor, and a tungsten precursor, followed by drying and calcining to produce a catalyst represented by the above Chemical Formula 1.

The method of mixing the aqueous solution of the precursors of $M^1$ and $M^2$ atoms, zirconium precursor, phosphorus precursor, and tungsten precursor in the catalyst of Chemical Formula 1 is not particularly limited. For example, the precursors may be sequentially introduced into the reactor one by one and mixed, or may be introduced at once and mixed. Most of all, in the case of introducing the zirconium precursor, the precursors of $M^1$ and $M^2$ atoms, and the tungsten precursor into the reactor, followed by introducing the phosphorus precursor compound, the precursors are well dissolved because the phosphorus precursor compound is added after the zirconium precursor, the precursors of $M^1$ and $M^2$ atoms, and the tungsten precursor are completely dissolved, and the catalyst yield may be increased because a stable crystal structure may be formed more easily.

In the step of mixing the precursors of the components, the amount of the catalyst formed may be increased by introducing a solvent into the reactor at first and adding the precursors thereto while stirring, by introducing a part of the precursors in the reactor and adding the rest of the precursors thereto while stirring, or by introducing all of the precursors into the reactor and stirring the mixture of the precursors. For example, it is possible that a solvent such as water and the like is introduced into the reactor at first and the precursors are successively or simultaneously added thereto in the reactor while stirring the solvent. For another example, it is possible that a part of the precursors is introduced into the reactor at first and the rest of the precursors are successively or simultaneously added thereto while stirring the same. For another example, it is possible that all of the precursors are successively or simultaneously introduced in the reactor to prepare a mixture, and the mixture is stirred. In all of above cases, the mixture of the precursors may be stirred even after all of the precursors are introduced into the reactor. Particularly, the stirring of the mixture may be carried out at the temperature of about 25 to 200 degrees Celsius (° C.) to facilitate the bond between metals.

Furthermore, the stirring may be carried out for a sufficient time to mix all of the precursors well to generate a large amount of precipitates. For example, the stirring may be carried out for about 3 to 48 h.

A step of precipitating the precursor compound of the catalyst represented by Chemical Formula 1 from the aqueous solution containing the precursor compounds of the respective components may be further included in the preparation method.

As the precursor used in the preparation method, various precursors known in the art of the present invention may be used. For non-restrictive examples, zirconyl chloride, zirconyl bromide, zirconyl iodide, zirconyl nitrate, and so on may be used as the zirconium precursor. In addition, an oxide of $M^1$ and $M^2$ metals, a hydroxide of $M^1$ and $M^2$ metals, a nitrate of $M^1$ and $M^2$ metals, an oxalate of $M^1$ and $M^2$ metals, a phosphate of $M^1$ and $M^2$ metals, a halide of $M^1$ and $M^2$ metals, and so on may be used as the precursors of $M^1$ and $M^2$ atoms. For example, $NH_4VO_3$, vanadium chloride, vanadium sulfate, and so on may be used as a vanadium precursor, $Fe(NO_3)_3$, a chloride or a nitrate of iron, and so on may be used as an iron precursor, $C_4H_4NNbO_9$ and so on may be used as a niobium precursor, and $Zn(NO_3)_2$ and so on may be used as a zinc precursor. In addition, one or more than two kinds of precursors may be used as the precursors of $M^1$ and $M^2$ atoms. For a non-restrictive example, a mixed precursor of a zinc precursor and an iron precursor, or a mixed precursor of a zinc precursor, iron precursor, and a vanadium precursor may be used together. Also, phosphoric acid, a phosphate in which one or more protons of phosphoric acid are substituted by cations of a Group 1 element, a Group 2 element, or a Group 13 element or by an ammonium cation, and so on may be used as the phosphorus precursor compound. As the tungsten precursor, ammonium meta-tungstate, ammonium para-tungstate, tungstic acid, tungsten blue oxide, tungsten trioxide, and so on may be used. The precursors may be anhydrides or hydrates. In addition, the precursors may be used in a proper content according to the ratio of atoms and atomic groups of Chemical Formula 1. For example, zirconium oxychloride ($ZrOCl.8H_2O$), zirconium oxynitrate ($ZrO(NO_3)_2.H_2O$), phosphoric acid ($H_3PO_4$), ammonium phosphate (($NH_4)_2HPO_4$), iron nitrate ($Fe(NO_3)_3.9H_2O$), zinc nitrate ($Zn(NO_3)_3.6H_2O$), ammonium metavanadate ($NH_4VO_3$), and ammonium metatungstate may be used as the precursors for the catalyst according to the present disclosure.

In the step of mixing the precursors, a proper solvent may be used for uniform mixing of the precursors. The solvent is not limited particularly, and water and the like may be used as a non-restrictive example.

The precursor compound of the catalyst represented by Chemical Formula 1 may be precipitated from the mixed aqueous solution of the precursors, and the preparation method may further include the step of filtering the precipitated catalyst precursor compound and washing it with water, an alcohol, or a mixture thereof. Particularly, the catalyst having a wider surface area may be prepared by washing the precipitate with an alcohol. The catalyst having a wide surface area may show much better catalytic activity and selectivity to acrolein in the dehydration reaction of glycerin.

The alcohol which may be used in the washing step may include an alkyl alcohol having 1 to 10 carbon atoms such as methanol, ethanol, propanol, butanol, pentanol, hexanol, and so on.

In addition, after mixing the aqueous solution of precursors, drying and calcining may be carried out to produce a catalyst represented by the above Chemical Formula 1. Herein, the drying may be carried out at a temperature of 25 to 200° C., for 3 to 48 h. Herein, the calcining may be carried out at a temperature of 250 to 750° C., for 3 to 48 h.

In the present disclosure, it is possible to further include a step of molding and assembling the calcined product after the drying and calcining step, or before the drying step. The above molding and assembling process may be performed by mixing with a coagulant containing a sol or a slurry and an alcohol in the form of a solution containing an inorganic metal component for improving the mechanical strength of the mixed oxide having low mechanical strength, and then extruding it. Examples of the inorganic metal component may include at least one type of filler such as silica, alumina, titania, zirconia, and the like. In the preparation method of a catalyst for dehydration of glycerin according to one embodiment, a catalyst may be formed by extruding a mixture of a mixed oxide and a coagulant to have better mechanical strength. The catalyst molded by this method may have superior strength compared with the case that the catalyst is used directly or supported on a support. Accordingly, the molded catalyst may maintain the reaction activity for a long period of time without generating internal pressure even when it is applied to an actual pilot process or a commercial process. The materials to be mixed may include at least one inorganic metal sol from the group consisting of silica sol, alumina sol, titania sol, and zirconia sol, and at least one alcohol selected from the group consisting of glycerin, isopropyl alcohol, diacetone alcohol, methanol, ethanol, and propanol.

The molded and assembled catalyst may be subjected to drying and calcining. Herein, the drying may be carried out at a temperature of 25 to 200° C., and for 3 to 48 h. Further, the calcining may be carried out at a temperature of 250 to 750° C., and for 3 to 48 h.

The preparation method of the catalyst may further include steps that are commonly applied in the art of the present invention, in addition to the steps described above.

According to another embodiment of the present disclosure, a production method of acrolein, including the step of dehydration of glycerin in the presence of the catalyst for dehydration of glycerin, is provided.

The production method of acrolein, for example, may provide acrolein by carrying out the dehydration reaction of glycerin in a continuous flow gas-phase reacting system in the presence of the catalyst.

Glycerin or a glycerin aqueous solution may be used as a reactant of the production method. In addition, an inert gas, or a gas mixture of an inert gas, and air or oxygen, may be used as a carrier gas for the reactant. In particular, the dehydration reaction may be carried out under the condition of a glycerin concentration of 25 to 75% by weight. Herein, the gas reactant may contain glycerin in an amount of 1 to 10 mol %, and may contain oxygen in an amount of 1 to 20 mol %.

In the production method of acrolein, the amount of the catalyst represented by Chemical Formula 1 may be appropriately controlled according to the amount and concentration of glycerin which is a reactant. For example, the catalyst may be filled at a weight hourly space velocity of 10 to 300 glycerin mmol/h·$g_{cat}$, preferably 10 to 100 glycerin mmol/h·$g_{cat}$, and more preferably 5 to 50 glycerin mmol/h·$g_{cat}$. If the amount of the catalyst is too small, the yield of the final acrylic acid may be lowered due to the decrease in the conversion of glycerin.

In the present disclosure, the glycerin reaction process may be carried out at a gas hourly space velocity (GHSV) of 100 to 5000 $h^{-1}$, preferably 250 to 3000 $h^{-1}$, and more preferably 500 to 1000 $h^{-1}$. Particularly, when the gas hourly space velocity (GHSV) increases in the glycerin reaction process, it means that the reactants which could be treated per unit time and per catalyst are increased. Therefore, the reaction at a high GHSV may have excellent catalytic activity. In addition, when the activity is high at a low reaction temperature, it means that catalytic activity of the catalyst is good. That is, since the amount of the catalyst used to obtain the same amount of product is small, a smaller reactor may be used. In addition, since the reaction at a low temperature uses less utilities, it can be said that the reaction is economical due to a low cost, and is excellent in terms of overall process efficiency.

In addition, the step of reacting glycerin may be carried out at a temperature of 250 to 350° C., and more preferably 280 to 320° C. Since the step of reacting glycerin is an endothermic reaction, it is preferable to carry out the reaction at a temperature within the above range in order to produce acrolein at a high conversion rate and selectivity to increase a yield of the final acrylic acid. If the reaction temperature is too low, the conversion rate of glycerin may be reduced, and if the reaction temperature is too high, the selectivity to acrolein may be reduced due to excessive side reactions.

In particular, when the dehydration reaction is carried out using the catalyst of the present disclosure, there are advantages that high catalytic activity, a high yield, and high selectivity to acrolein and acrylic acid are exhibited, and a continuous process may be carried out due to the characteristic that the generated coke carbon is burned and removed. The preferred process conditions for the dehydration reaction of glycerin are continuous operations, and if the reaction temperature is low and the reactor size is small, the process will be better. The crucial reason why the process has not yet been commercialized is that the process cannot be operated continuously, and requires periodic decoking processes to remove coke carbon. Therefore, the catalyst of the present disclosure may be used with the operating conditions which enable effective removal of coke carbon to perform the glycerin dehydration reaction in a continuous process, while maintaining high catalytic activity.

Further, after performing the dehydration reaction, a partial oxidation reaction of acrolein from the product obtained from the dehydration reaction may be performed to finally convert the acrolein produced through the dehydration reaction of glycerin to acrylic acid.

The production method of acrolein may further include steps that are commonly applied in the art of the present invention, in addition to the steps described above.

Meanwhile, the production method of acrolein according to the present disclosure may maintain a glycerin conversion of at least 90% measured at about 300 h or more after the initiation of the reaction, and may have selectivity to one or more products selected from the group consisting of acrolein and acrylic acid of more than 35%.

Also, after performing the glycerin dehydration reaction using the catalyst of the present disclosure, the $CO_x$ value measured by GC analysis on the liquid product and the gaseous product may be about 40% or less, or 1% to 40%, preferably 36% or less, and more preferably 35% or less. The $CO_x$ value is a value indicating the degree of oxidation of the coke carbon or the reaction product. If it is too large, it means that there is an adverse effect that the reaction product is also oxidized in addition to the coke carbon. Particularly, it can be understood that the best effect is obtained if the reaction activity is maintained while maintaining the low $CO_x$ value.

Hereinafter, preferred embodiments of the present invention will be described in detail. However, these examples are for illustrative purposes only, and the invention is not intended to be limited by these examples.

EXAMPLES

Preparation Example 1

Preparation of a Catalyst for Dehydration of Glycerin

An aqueous solution was prepared by adding 12.208 g of $ZrOCl_2$, a zirconium precursor, to 150 mL of distilled water. 0.225 g of $Zn(NO_3)_2 \cdot 6H_2O$, a zinc precursor, and 0.933 g of $H_{26}N_6O_{40}W_{12}$, a tungsten precursor, were added to the aqueous solution and the mixture was stirred for about 30 min to 1 h. After preparing another aqueous solution by adding 8.714 g of $NH_4H_2PO_4$, a phosphorus precursor compound, to 150 mL of distilled water, the phosphorus precursor aqueous solution was added to the zirconium aqueous solution prepared above and the mixture was stirred overnight at a temperature of about 95° C.

Thereafter, the precipitate settled from the aqueous solution was washed with ethanol, dried at 100° C. for 12 h, and calcined at 700° C. for 6 h to obtain $ZrZn_{0.02}W_{0.1}P_2H_xO_y$, a catalyst for dehydration of glycerin.

Preparation Example 2

Preparation of a Catalyst for Dehydration of Glycerin

An aqueous solution was prepared by adding 10.986 g of $ZrOCl_2$, a zirconium precursor, to 150 mL of distilled water. 1.54 g of $Fe(NO_3)_3 \cdot 9H_2O$, an iron precursor, and 0.933 g of $H_{26}N_6O_{40}W_{12}$, a tungsten precursor, were added to the aqueous solution and the mixture was stirred for about 30 min to 1 h. After preparing another aqueous solution by adding 8.714 g of $NH_4H_2PO_4$, a phosphorus precursor compound, to 150 mL of distilled water, the phosphorus precursor aqueous solution was added to the zirconium aqueous solution prepared above and the mixture was stirred overnight at a temperature of about 95° C.

Thereafter, $Zr_{0.9}Fe_{0.1}W_{0.1}P_2H_xO_y$, a catalyst for dehydration of glycerin, was obtained according to the same method as in Preparation Example 1.

Preparation Example 3

Preparation of a Catalyst for Dehydration of Glycerin $Zr_{0.9}V_{0.1}W_{0.1}P_2H_xO_y$, a catalyst for dehydration of glycerin, was obtained according to the same method as in Preparation Example 2, except that 0.448 g of $NH_4VO_3$, a vanadium precursor, was used instead of the iron precursor.

Preparation Example 4

Preparation of a Catalyst for Dehydration of Glycerin $Zr_{0.9}Nb_{0.02}Fe_{0.1}W_{0.1}P_2H_xO_y$, a catalyst for dehydration of glycerin, was obtained according to the same method as in Preparation Example 2, except that 0.230 g of ammonium niobate(V) oxalate hydrate ($C_4H_4NNbO_9 \cdot xH_2O$), a niobium precursor, was additionally added.

Preparation Example 5

Preparation of a Catalyst for Dehydration of Glycerin $Zr_{0.9}Zn_{0.02}Fe_{0.1}W_{0.1}P_2H_xO_y$, a catalyst for dehydration of glycerin, was obtained according to the same method as in Preparation Example 2, except that 0.225 g of $Zn(NO_3)_2 \cdot 6H_2O$, a zinc precursor, was additionally added.

Preparation Example 6

Preparation of a Catalyst for Dehydration of Glycerin $Zr_{0.9}Zn_{0.02}V_{0.1}W_{0.1}P_2H_xO_y$, a catalyst for dehydration of glycerin, was obtained according to the same method as in Preparation Example 3, except that 0.225 g of $Zn(NO_3)_2 \cdot 6H_2O$, a zinc precursor, was additionally added.

Preparation Example 7

Preparation of a Catalyst for Dehydration of Glycerin

An aqueous solution was prepared by adding 9.766 g of $ZrOCl_2$, a zirconium precursor, to 150 mL of distilled water. 0.225 g of $Zn(NO_3)_2 \cdot 6H_2O$, a zinc precursor, 1.54 g of $Fe(NO_3)_3 \cdot 9H_2O$, an iron precursor, 0.448 g of $NH_4VO_3$, a vanadium precursor, and 0.933 g of $H_{26}N_6O_{40}W_{12}$, a tungsten precursor, were added to the aqueous solution and the mixture was stirred for about 30 min to 1 h. After preparing another aqueous solution by adding 8.714 g of $NH_4H_2PO_4$, a phosphorus precursor compound, to 150 mL of distilled water, the phosphorus precursor aqueous solution was added to the zirconium aqueous solution prepared above and the mixture was stirred overnight at a temperature of about 95° C.

Thereafter, $Zr_{0.8}Zn_{0.02}(FeV)_{0.1}W_{0.1}P_2H_xO_y$, a catalyst for dehydration of glycerin, was obtained according to the same method as in Preparation Example 1.

Preparation Example 8

Preparation of a Catalyst for Dehydration of Glycerin

An aqueous solution was prepared by adding 9.766 g of $ZrOCl_2$, a zirconium precursor, to 150 mL of distilled water. 0.225 g of $Zn(NO_3)_2 \cdot 6H_2O$, a zinc precursor, 3.08 g of $Fe(NO_3)_3 \cdot 9H_2O$, an iron precursor, and 0.933 g of $H_{26}N_6O_{40}W_{12}$, a tungsten precursor, were added to the aqueous solution and the mixture was stirred for about 30 min to 1 h. After preparing another aqueous solution by adding 8.714 g of $NH_4H_2PO_4$, a phosphorus precursor compound, to 150 mL of distilled water, the phosphorus precursor aqueous solution was added to the zirconium aqueous solution prepared above and the mixture was stirred overnight at a temperature of about 95° C.

Thereafter, $Zr_{0.8}Zn_{0.02}Fe_{0.2}W_{0.1}P_2H_xO_y$, a catalyst for dehydration of glycerin, was obtained according to the same method as in Preparation Example 1.

Preparation Example 9

Preparation of a Catalyst for Dehydration of Glycerin $Zr_{0.8}Zn_{0.02}V_{0.2}W_{0.1}P_2H_xO_y$, a catalyst for dehydration of glycerin, was obtained according to the same method as in Preparation Example 8, except that 0.896 g of $NH_4VO_3$, a vanadium precursor, was used instead of the iron precursor.

Preparation Example 10

Preparation of a Molded and Assembled Catalyst for Dehydration of Glycerin

An aqueous solution was prepared by adding 12.208 g of $ZrOCl_2$, a zirconium precursor, to 150 mL of distilled water. 0.225 g of $Zn(NO_3)_2 \cdot 6H_2O$, a zinc precursor, and 0.933 g of $H_{26}N_6O_{40}W_{12}$, a tungsten precursor, were added to the aqueous solution and the mixture was stirred for about 30 min to 1 h. After preparing another aqueous solution by adding 8.714 g of $NH_4H_2PO_4$, a phosphorus precursor compound, to 150 mL of distilled water, the phosphorus precursor aqueous solution was added to the zirconium aqueous solution prepared above and the mixture was stirred overnight at a temperature of about 95° C.

Thereafter, the precipitate settled from the aqueous solution was washed with ethanol, dried at 100° C. for 12 h, and calcined at 700° C. for 6 h.

The calcined product was molded and assembled, dried at 100° C. for 12 h and then calcined at 700° C. for 6 h to obtain $ZrZn_{0.02}W_{0.1}P_2H_xO_y$, a molded and assembled catalyst for dehydration of glycerin. Herein, the catalyst which is shaped and assembled to be extruded was in the form of a cylinder, and had a diameter of 0.5 cm and a length of 0.5-1.5 cm.

Preparation Example 11

Preparation of a Molded and Assembled Catalyst for Dehydration of Glycerin $Zr_{0.9}Zn_{0.02}Fe_{0.1}W_{0.1}P_2H_xO_y$, a molded and assembled catalyst for dehydration of glycerin, was obtained according to the same method as in Preparation Example 10, except that 1.54 g of $Fe(NO_3)_3 \cdot 9H_2O$, an iron precursor, was additionally added.

Preparation Example 12

Preparation of a Molded and Assembled Catalyst for Dehydration of Glycerin $Zr_{0.9}Zn_{0.02}V_{0.1}W_{0.1}P_2H_xO_y$, a molded and assembled catalyst for dehydration of glycerin, was obtained according to the same method as in Preparation Example 10, except that 0.448 g of $NH_4VO_3$, a vanadium precursor, was used instead of the iron precursor.

Preparation Example 13

Preparation of a Molded and Assembled Catalyst for Dehydration of Glycerin $Zr_{0.95}Zn_{0.02}V_{0.05}W_{0.1}P_2H_xO_y$, a molded and assembled catalyst for dehydration of glycerin, was obtained according to the same method as in Preparation Example 10, except that 0.224 g of $NH_4VO_3$, a vanadium precursor, was used instead of the iron precursor.

Comparative Preparation Example 1

Preparation of a Catalyst for Dehydration of Glycerin

An aqueous solution was prepared by adding 12.208 g of $ZrOCl_2$, a zirconium precursor, to 150 mL of distilled water. After preparing another aqueous solution by adding 8.714 g of $NH_4H_2PO_4$, a phosphorus precursor compound, to 150 mL of distilled water, the phosphorus precursor aqueous solution was added to the zirconium aqueous solution prepared above and the mixture was stirred overnight at a temperature of about 95° C.

Thereafter, the precipitate settled from the aqueous solution was washed with ethanol, dried at 100° C. for 12 h, and calcined at 700° C. for 6 h to obtain ZrP, a catalyst for dehydration of glycerin.

Comparative Preparation Example 2

Preparation of a Catalyst for Dehydration of Glycerin

An aqueous solution was prepared by adding 3.12 g of $H_3BO_3$, a boronic acid, to 150 mL of distilled water, and maintained at a temperature of 60° C. or more. After preparing another aqueous solution by adding 5.88 g of $H_3PO_4$, a phosphoric acid, to 50 mL of distilled water, the phosphorus precursor aqueous solution was added to the boron aqueous solution prepared above. Thereafter, the mixture was supported on $SiO_2$ which is a support, dried at 100° C. for 12 h, and then calcined at 500° C. for 6 h to obtain 11.08 wt % $BPO_4/SiO_2$, a catalyst for dehydration of glycerin.

Example 1 to 17 and Comparative Example 1 to 2

Dehydration Reaction of Glycerin

A dehydration reaction of glycerin was carried out using the catalyst prepared according to Preparation Examples 1 to 13 and Comparative Preparation Examples 1 and 2, and the reaction apparatus as shown in FIG. 1.

The production of acrolein by dehydration of glycerin was carried out by using a continuous flow fixed bed reactor. After installing the continuous flow fixed bed reactor in an electric furnace, the catalyst prepared according to Preparation Examples 1 to 13 and Comparative Preparation Examples 1 to 2 was put in the reactor. As shown in the following Table 1, when the reaction was carried out using the reactor 1 and reactor 2, the temperature of the reactor was raised to about 280-350° C., while flowing nitrogen and air as a carrier gas and a coke carbon oxidizing gas, at a velocity of 10-1000 mL/min, respectively. Thereafter, the temperature was maintained for a period of time for maintaining the steady state of the reaction line.

Then, a glycerin aqueous solution (28.08-75.0 wt % in $H_2O$; 7.1 mol %) was introduced into the reactor at a constant rate to the amount of the filled catalyst, and the dehydration reaction of glycerin was carried out. Herein, the detailed reactor conditions are shown in Table 1 below.

TABLE 1

| | Reactor 1 | Reactor 2 |
|---|---|---|
| | Reactor type | |
| | Stainless steel reactor length of 1M, diameter of 1 inch (1") | Stainless steel reactor length of 30 cm, diameter of ⅜ inch (⅜") |
| Reaction pressure (atm) | 1 | 1 |
| Reaction temperature (° C.) | 280-350 | 280-350 |
| Reaction time (h) | 1-300 | 1-50 |
| Concentration of glycerin (wt %) | 28.08-75.0 | 28.08-75.0 |
| Injected gas | $N_2$ + air | $N_2$ + air |
| GHSV (/h) | 700-1500 | 6500-28000 |
| Amount of catalyst (g) | 50 | 0.3-0.6 |

The glycerin aqueous solution was vaporized in a vaporizer, heated in a pre-heater region, and injected into a stainless-steel reactor filled with experimental catalysts at the reaction temperature to carry out the dehydration reaction. The products produced as a result of the reaction were condensed, and liquid and gaseous products were respectively analyzed by gas chromatography (GC).

Specific analysis methods are divided into liquid product analysis and gaseous product analysis. The liquid product is a value indicating the liquid product value by analyzing the condensed liquid product with a GC-FID detector, and the gaseous product is a value indicating the value of gaseous products by analyzing the gas product with a GC-TCD detector. The reason for the gaseous analysis in addition to the liquid analysis is to confirm the conversion of C component to CO and $CO_2$ in response to air. For catalysts that only analyze liquid products, $CO_x$ which was converted to gas should be considered. The $CO_x$ value is time dependent, and is about 1% to 34%.

In order to make a comparative comparison between the catalysts analyzing only the liquid product and the catalysts analyzing both the liquid and the gaseous products, activity values of the catalysts analyzing both the liquid and the gaseous products are shown in Examples 13 and 14, and activity values of the catalysts analyzing only the liquid product are shown in Examples 11 and 12.

The detailed process conditions for the dehydration of glycerin of Examples 1 to 12 and Comparative Example 1 performed using the catalysts prepared according to Preparation Examples 1 to 11 and Comparative Preparation Example 1 are as shown in Table 2 below.

TABLE 2

| | Reactor | Catalyst | Injected gas | Concentration of glycerin (wt %) | Reaction temperature (° C.) | Reaction time (h) |
|---|---|---|---|---|---|---|
| Example 1 | Reactor 2 | $ZrZn_{0.02}W_{0.1}P_2H_xO_y$ | $N_2$ + air | 28.08 | 282 | 3/5/24 |
| Example 2 | Reactor 2 | $Zr_{0.9}Fe_{0.1}W_{0.1}P_2H_xO_y$ | $N_2$ + air | 28.08 | 282 | 3/5/24 |
| Example 3 | Reactor 2 | $Zr_{0.9}V_{0.1}W_{0.1}P_2H_xO_y$ | $N_2$ + air | 28.08 | 282 | 3/5/30 |
| Example 4 | Reactor 2 | $Zr_{0.9}Nb_{0.02}Fe_{0.1}W_{0.1}P_2H_xO_y$ | $N_2$ + air | 28.08 | 282 | 3/5/28 |
| Example 5 | Reactor 2 | $Zr_{0.9}Zn_{0.02}Fe_{0.1}W_{0.1}P_2H_xO_y$ | $N_2$ + air | 28.08 | 282 | 3/5/24 |
| Example 6 | Reactor 2 | $Zr_{0.9}Zn_{0.02}V_{0.1}W_{0.1}P_2H_xO_y$ | $N_2$ + air | 28.08 | 282 | 3/5/24 |
| Example 7 | Reactor 2 | $Zr_{0.9}Zn_{0.02}V_{0.1}W_{0.1}P_2H_xO_y$ | $N_2$ + air | 50 | 280 | 3/5/50 |
| Example 8 | Reactor 2 | $Zr_{0.8}Zn_{0.02}(FeV)_{0.1}W_{0.1}P_2H_xO_y$ | $N_2$ + air | 28.08 | 282 | 3/5/24 |

TABLE 2-continued

|  | Reactor | Catalyst | Injected gas | Concentration of glycerin (wt %) | Reaction temperature (° C.) | Reaction time (h) |
|---|---|---|---|---|---|---|
| Example 9[*] | Reactor 1 | $ZrZn_{0.02}W_{0.1}P_2H_xO_y$ | $N_2$ + air | 28.08 | 280 | 4/190/290 |
| Example 10[*] | Reactor 1 | $Zr_{0.9}Zn_{0.02}Fe_{0.1}W_{0.1}P_2H_xO_y$ | $N_2$ + air | 28.08 | 282 | 4/188/234 |
| Example 11[**] | Reactor 2 | $Zr_{0.8}Zn_{0.02}Fe_{0.2}W_{0.1}P_2H_xO_y$ | $N_2$ + air | 28.08 | 345 | 3/5/50 |
| Example 12[***] | Reactor 2 | $Zr_{0.8}Zn_{0.02}V_{0.2}W_{0.1}P_2H_xO_y$ | $N_2$ + air | 28.08 | 345 | 3/5/50 |
| Comparative Example 1 | Reactor 2 | ZrP | $N_2$ + air | 28.08 | 281 | 3/5/19 |

[*]In Examples 9 and 10, a reaction experiment was carried out using a molded and assembled catalyst.
[**]Example 11 is an analysis of only the liquid product from Example 13.
[***]Example 12 is an analysis of only the liquid product from Example 14.

The analytical results of the liquid product after the dehydration reaction of glycerin of Examples 1 to 12 and Comparative Example 1 are as shown in Table 3 below.

TABLE 3

|  | Conversion ratio of glycerin (%) | Selectivity to acrolein + acrylic acid (%) | Comparative selectivity 1 | Comparative selectivity 2 |
|---|---|---|---|---|
| Example 1 | 19.8/37.8/34.3 | 58.3/57.3/73.3 | 0.14/0.19/0.11 | 0.58/0.56/0.26 |
| Example 2 | 26.7/42.7/21.2 | 58.1/66.9/70.2 | 0.03/0.06/0.05 | 0.69/0.44/0.38 |
| Example 3 | 16.2/51.5/22.5 | 49.1/56.9/66.4 | 0.19/0.17/0.09 | 0.85/0.59/0.42 |
| Example 4 | 17.5/42.4/33.5 | 53.5/65.9/74.8 | 0.07/0.05/0.07 | 0.80/0.47/0.27 |
| Example 5 | 12.1/66.3/38.8 | 57.6/69.8/74.5 | 0.09/0.06/0.07 | 0.65/0.38/0.28 |
| Example 6 | 14.9/53.5/44.4 | 54.7/64.1/69.8 | 0.13/0.11/0.08 | 0.70/0.45/0.36 |
| Example 7 | 99.9/100/98.1 | 54.3/52.8/48.7 | 0.11/0.11/0.14 | 0.08/0.10/0.20 |
| Example 8 | 22.2/56.4/36.8 | 51.0/64.1/59.2 | 0.08/0.07/0.07 | 0.88/0.49/0.62 |
| Example 9[*] | 100/100/95.2 | 87.4/88.3/72.7 | 0.01/0.04/0.06 | 0.13/0.10/0.32 |
| Example 10[*] | 99.9/99.9/99.3 | 70.2/75.5/75.1 | 0.09/0.16/0.08 | 0.33/0.51/0.45 |
| Example 11[**] | 37.2/24.4/98.4 | 63.7/61.9/65.3 | 0.19/0.11/0.08 | 0.38/0.51/0.45 |
| Example 12[***] | 37.2/50.8/94.7 | 43.9/56.2/60.2 | 0.18/0.16/0.12 | 0.38/0.51/0.45 |
| Comparative Example 1 | 13.9/28.3/29.6 | 43.9/65.1/78.2 | 0.10/0.07/0.07 | 1.17/0.47/0.21 |

Conversion ratio = (amount of glycerin in the reactant − amount of glycerin in the product)/amount of glycerin in the reactant
Selectivity = amount of product/(amount of glycerin in the reactant − amount of glycerin in the product)
Comparative selectivity 1 = (hydroxyacetone + acetic acid) selectivity/(acrolein + acrylic acid) selectivity
Comparative selectivity 2 = (Total product − hydroxyacetone − acetic acid − acrolein − acrylic acid) selectivity/(acrolein + acrylic acid) selectivity
[*]In Example 9 and 10, a reaction experiment was carried out using a molded and assembled catalyst.
[**]Example 11 is an analysis of only the liquid product from Example 13.
[***]Example 12 is an analysis of only the liquid product from Example 14.

The detailed process conditions for the dehydration of glycerin of Examples 13 to 17 and Comparative Example 2 performed using the catalysts prepared according to Preparation Examples 8, 9, 12, 13, and Comparative Preparation Example 2 are as shown in Table 4 below.

TABLE 4

|  | Reactor | Catalyst | Injected gas | Concentration of glycerin (wt %) | Reaction temperature (° C.) | Reaction time (h) |
|---|---|---|---|---|---|---|
| Example 13[*] | Reactor 2 | $Zr_{0.8}Zn_{0.02}Fe_{0.2}W_{0.1}P_2H_xO_y$ | $N_2$ + air | 28.08 | 345 | 3/5/50 |
| Example 14[**] | Reactor 2 | $Zr_{0.8}Zn_{0.02}V_{0.2}W_{0.1}P_2H_xO_y$ | $N_2$ + air | 28.08 | 345 | 3/5/50 |
| Example 15[***] | Reactor 1 | $Zr_{0.95}Zn_{0.02}V_{0.05}W_{0.1}P_2H_xO_y$ | $N_2$ + air | 50 | 312 | 3/63/129 |
| Example 16[***] | Reactor 1 | $Zr_{0.9}Zn_{0.02}V_{0.1}W_{0.1}P_2H_xO_y$ | $N_2$ + air | 50 | 284 | 3/70/274 |
| Example 17[***] | Reactor 1 | $Zr_{0.9}Zn_{0.02}V_{0.1}W_{0.1}P_2H_xO_y$ | $N_2$ + air | 75 | 285 | 2/65/210 |
| Comparative Example 2 | Reactor 2 | 11.08 wt % $BPO_4/SiO_2$ | $N_2$ + air | 28.08 | 275 | 1/5/24 |

[*]Example 13 is an analysis of both the liquid and the gaseous product concerning Example 11.
[**]Example 14 is an analysis of both the liquid and the gaseous product concerning Example 12.
[***]In Examples 15 to 17, a reaction experiment was carried out using a molded and assembled catalyst.

The analytical results of the liquid and gaseous product after the dehydration reaction of glycerin of Examples 13 to 17 and Comparative Example 2 are as shown in Table 3 below.

TABLE 5

|  | Conversion ratio of glycerin (%) | Selectivity to acrolein + acrylic acid (%) | Comparative selectivity 1 | $CO_x$ (%) | Comparative selectivity 2 |
|---|---|---|---|---|---|
| Example 13* | 37.2/24.4/98.4 | 60.6/58.7/51.8 | 0.18/0.10/0.07 | 4.9/5.1/20.6 | 0.32/0.42/0.12 |
| Example 14** | 37.2/50.8/94.7 | 44.0/56.1/39.6 | 0.25/0.16/0.12 | 1.1/1.7/34.2 | 1.02/0.52/0.09 |
| Example 15*** | 97.9/99.7/90.6 | 63.4/51.9/55.0 | 0.09/0.16/0.11 | 10.9/16.7/24.1 | 0.29/0.50/0.39 |
| Example 16*** | 99.9/99.9/99.4 | 42.7/51.6/47.0 | 0.21/0.13/0.26 | 32.1/16.0/11.1 | 0.22/0.41/0.55 |
| Example 17*** | 99.9/99.9/99.7 | 36.3/56.1/48.2 | 1.36/0.27/0.36 | 12.4/19.4/27.3 | 0.05/0.12/0.09 |
| Comparative Example 2 | 3.3/1.0/0.8 | 54.4/13.3/12.4 | 0.43/1.28/0.41 | 0.18/0.25/0.69 | 0.43/5.34/6.61 |

Conversion ratio = (amount of glycerin in the reactant – amount of glycerin in the product)/amount of glycerin in the reactant
Selectivity = amount of product/(amount of glycerin in the reactant – amount of glycerin in the product)
Comparative selectivity 1 = (hydroxyacetone + acetic acid) selectivity/(acrolein + acrylic acid) selectivity
Comparative selectivity 2 = (Total product – hydroxyacetone – acetic acid – acrolein – acrylic acid) selectivity/(acrolein ± acrylic acid) selectivity
*Example 13 is an analysis of both the liquid and the gaseous product concerning Example 11.
**Example 14 is an analysis of both the liquid and the gaseous product concerning Example 12.
***In Examples 15 to 17, a reaction experiment was carried out using a molded and assembled catalyst.

As shown in Table 3 and Table 5, in the case of Examples 1 to 17 in which the dehydration reaction of glycerin was carried out using the catalysts of Preparation Examples 1 to 13 according to the present disclosure, it was confirmed that the dehydration reaction process of glycerin may be continuously operated using a fixed bed reactor which has been used commercially, and acrolein and/or acrylic acid may be obtained from glycerin in a high yield.

On the other hand, FIG. 2 and FIG. 3 are graphs showing the conversion of glycerin, the selectivity to acrolein+acrylic acid, and the yield of $CO_x$, when glycerin was continuously reacted for a long period of time using the molded and assembled catalysts of Preparation Examples 12 and 13 according to Examples 16 and 17. In particular, when the conventional catalyst was used as in Comparative Example 2, the conversion ratio was remarkably reduced in 5 h due to the formation of coke carbon on the catalyst even though 28.08 wt % solution of glycerin was used as the reactant. However, according to Examples 16 and 17 of the present disclosure, it can be understood that the catalyst has excellent catalytic performance, because it can keep the reaction performance for 200 h or more by reducing the production of coke carbon as much as possible even when a high concentration of 50 wt % or 75 wt % glycerin aqueous solution is used. In addition, it can be understood that the $BPO_4$ catalyst of Comparative Example 2, like conventionally known heteropoly acids, cannot be used for commercialized process, because excessive coke carbon is produced in a short time.

Particularly, it was confirmed that the liquid phase results of Examples 9 and 10, in which the reaction experiment was carried out using the molded and assembled catalyst, showed a significantly higher level of selectivity to acrolein. Further, referring to the analysis of gaseous products from liquid phase results (Table 3) and liquid phase and gaseous phase results (Table 5) of Examples 11, 12, 13, 14, 15, and 16, it can be understood that $CO_x$ occurs considerably with time, the removal of carbon occurs, and continuous operation for more than 100 h is possible. Accordingly, it can be said that the present disclosure has an excellent feature that it can be operated continuously for a long time under a high space velocity condition.

The invention claimed is:

1. A catalyst for dehydration of glycerin represented by the following Chemical Formula 1:

$$Zr_a(M^1)_b(M^2)_cW_dP_eH_xO_y \quad \text{[Chemical Formula 1]}$$

wherein, in Chemical Formula 1, $M^1$ and $M^2$ are the same as or different from each other, and are independently V, Fe, Nb, Zn, or a combination thereof;

a, b, c, d, and e represent ratios of atoms, wherein a is 0.5 to 1, b is 0.01 to 0.3, c is 0.01 to 0.3, d is 0.01 to 0.3, e is 1 to 5, b/a is 0.01 to 0.6, c/a is 0.01 to 0.6, d/a is 0.01 to 0.6, and e/a is 0.1 to 10; and x and y are values determined according to a bonding state of crystallization water, and are independently 0 to 10.

2. The catalyst for dehydration of glycerin according to claim 1, wherein the catalyst is $ZrZn_{0.02}W_{0.1}P_2H_xO_y$, $Zr_{0.9}Fe_{0.1}W_{0.1}P_2H_xO_y$, $Zr_{0.9}V_{0.1}W_{0.1}P_2H_xO_y$, $Zr_{0.9}Nb_{0.02}Fe_{0.1}W_{0.1}P_2H_xO_y$, $Zr_{0.9}Zn_{0.02}Fe_{0.1}W_{0.1}P_2H_xO_y$, $Zr_{0.9}Zn_{0.02}V_{0.1}W_{0.1}P_2H_xO_y$, $Zr_{0.8}Zn_{0.02}(FeV)_{0.1}W_{0.1}P_2H_xO_y$, $Zr_{0.8}Zn_{0.02}Fe_{0.2}W_{0.1}P_2H_xO_y$, $Zr_{0.8}Zn_{0.02}V_{0.2}W_{0.1}P_2H_xO_y$, or $Zr_{0.95}Zn_{0.02}V_{0.05}W_{0.1}P_2H_xO_y$, x is 2 to 6, and y is 1 to 3.

3. A preparation method of a catalyst for dehydration of glycerin, comprising the step of mixing one or more precursors selected from the group consisting of precursors of V, Fe, Nb, and Zn, a zirconium precursor, a phosphorus precursor, and a tungsten precursor, followed by drying and calcining to produce a catalyst represented by the following Chemical Formula 1:

$$Zr_a(M^1)_b(M^2)_cW_dP_eH_xO_y \quad \text{[Chemical Formula 1]}$$

wherein, in Chemical Formula 1, $M^1$ and $M^2$ are the same as or different from each other, and are independently V, Fe, Nb, Zn, or a combination thereof;

a, b, c, d, and e represent ratios of atoms, wherein a is 0.5 to 1, b is 0.01 to 0.3, c is 0.01 to 0.3, d is 0.01 to 0.3, e is 1 to 5, b/a is 0.01 to 0.6, c/a is 0.01 to 0.6, d/a is 0.01 to 0.6, and e/a is 0.1 to 10; and x and y are values determined according to a bonding state of crystallization water, and are independently 0 to 10.

4. The preparation method of a catalyst for dehydration of glycerin according to claim 3, wherein the drying is carried out at a temperature of 25 to 200° C.

5. The preparation method of a catalyst for dehydration of glycerin according to claim 3, wherein the drying is carried out for 3 to 48 hours.

6. The preparation method of a catalyst for dehydration of glycerin according to claim 3, wherein the calcining is carried out at a temperature of 250 to 750° C.

7. The preparation method of a catalyst for dehydration of glycerin according to claim 3, wherein the calcining is carried out for 3 to 48 hours.

8. The preparation method of a catalyst for dehydration of glycerin according to claim 3, wherein the mixture is stirred for 3 to 48 hours.

9. The preparation method of a catalyst for dehydration of glycerin according to claim 3, wherein the precursor compound of the catalyst represented by Chemical Formula 1 is precipitated from the mixed aqueous solution, and the precipitated catalyst precursor compound is filtered and washed with water or an alcohol, followed by drying and calcining.

10. A production method of acrolein, comprising the step of dehydration of glycerin in the presence of the catalyst for dehydration of glycerin according to claim 1.

* * * * *